United States Patent [19]

Shapiro

[11] Patent Number: 4,653,514
[45] Date of Patent: Mar. 31, 1987

[54] DEVICE FOR STRENGTHENING THE VAGINAL MUSCLES

[75] Inventor: Seymour W. Shapiro, Lowell, Ind.

[73] Assignee: Bivona, Inc., Gary, Ind.

[21] Appl. No.: 615,052

[22] Filed: May 29, 1984

Related U.S. Application Data

[63] Continuation of Ser. No. 219,241, Dec. 22, 1980, abandoned.

[51] Int. Cl.$^4$ ............................................. A61B 5/00
[52] U.S. Cl. .................................... 128/778; 272/135
[58] Field of Search ................. 128/778, 344, 207.15, 128/246, 349 B, DIG. 21, 25 R, 79, 341, 748, 348.1, 356; 272/93, 135; 604/96

[56] References Cited

U.S. PATENT DOCUMENTS

| | | | |
|---|---|---|---|
| 2,507,858 | 5/1950 | Kegel | 128/778 |
| 2,839,050 | 6/1958 | Sokol | 128/778 |
| 3,640,282 | 2/1972 | Kamen | 604/96 |
| 3,726,273 | 4/1973 | Cole | 128/778 |
| 3,799,173 | 3/1974 | Kamen | 604/96 |
| 3,882,852 | 5/1975 | Sinnreich | 128/344 |
| 3,889,685 | 6/1975 | Miller | 128/344 |
| 4,048,985 | 9/1977 | Sasse | 128/778 |
| 4,050,449 | 9/1977 | Castellana | 128/778 |
| 4,270,541 | 6/1981 | Okamoto et al. | 128/344 |

Primary Examiner—Richard C. Pinkham
Assistant Examiner—T. Brown
Attorney, Agent, or Firm—Emrich & Dithmar

[57] ABSTRACT

Device for use in exercising the vaginal muscles, embodying a cuffed rod for insertion into the vagina, the cuff being normally yieldingly inflated for affording a yielding resistive force, but being collapsible for insertion into the vagina. A volume displacement indicator is operatively connected to the cuff for measuring the amount of air flow from within the cuff resulting from the collapse of the cuff due to the contraction of the vaginal muscles.

7 Claims, 8 Drawing Figures

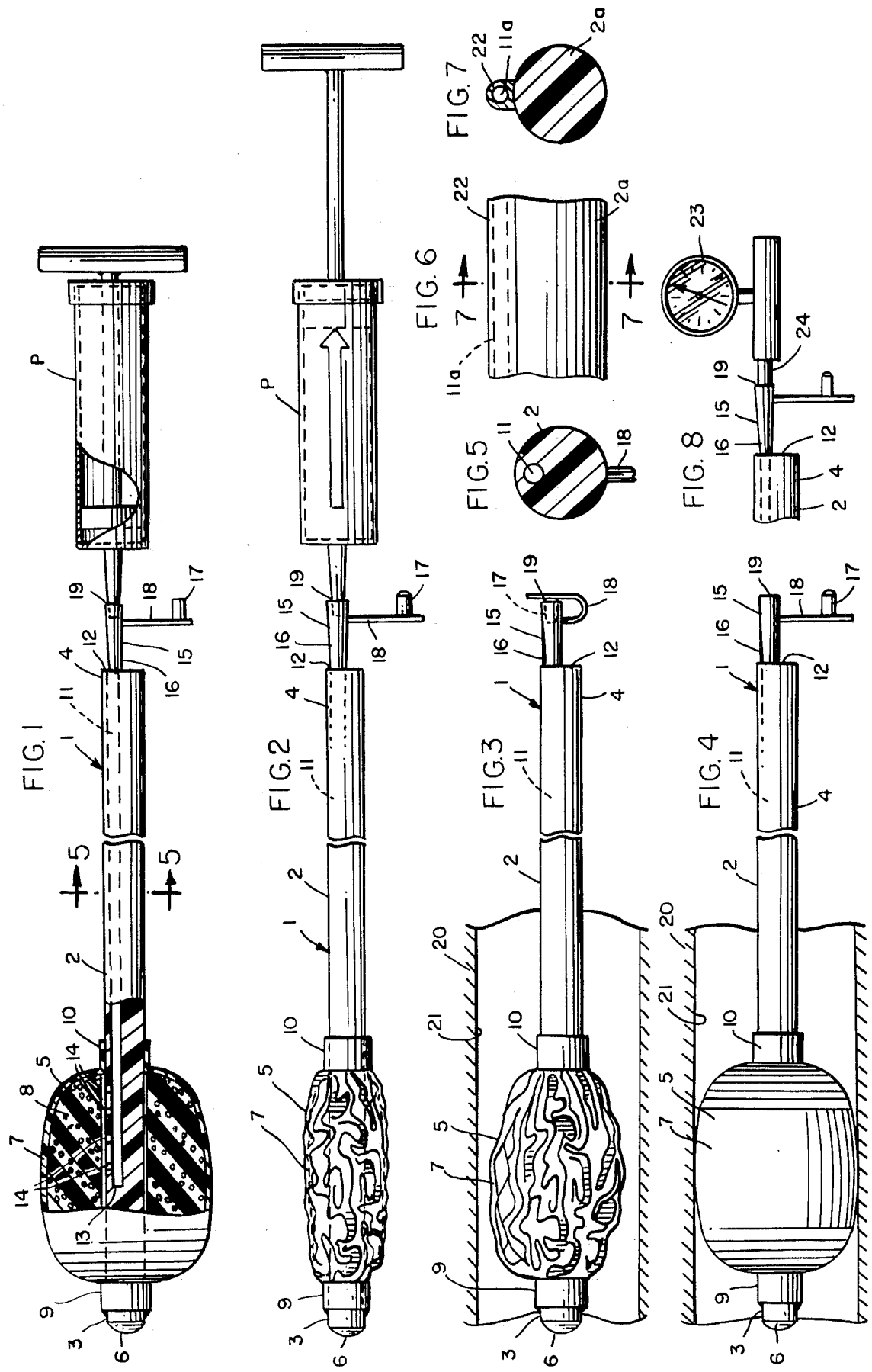

DEVICE FOR STRENGTHENING THE VAGINAL MUSCLES

This application is a continuation of application Ser. No. 219,241 filed 12-22-80, (now abandoned).

BACKGROUND OF THE INVENTION

This invention relates to devices for exercising the vaginal muscles.

The primary object of the present invention is to afford a novel device for use in exercising the vaginal muscles of a female.

Another object is to afford a novel device of the aforementioned type which may be readily inserted into the vagina of a female.

A further object is to afford a novel device of the aforementioned type, the parts of which are constituted and arranged in a novel and expeditious manner effective to protect the female against injury during insertion thereof into the vagina and during use thereof in the exercising of the vaginal muscles.

Weakness of the muscles of the pelvic floor is common among the adult female population, and, particularly, among those who have borne children. Advanced degrees of weakness of these muscles culminate in loss of support of the bladder, urethra, rectum and uterus.

Exercise is a well established means of obtaining and maintaining muscle fitness. Exercises may be classified into passive, active and resistive categories. Resistive exercises require the use of muscles against a force which, commonly, is relatively small at the beginning of an exercise program and gradually increases as the muscle tone and strength increases.

The pelvic floor muscles support the vaginal walls of a female. It is an important object of the present invention to afford a novel device for use in resistive exercising of these muscles.

Another object of the present invention is to afford a novel device of the aforementioned type wherein the resistive force thereof increases with increases in the tone and strength of the muscles.

Exercise devices for insertion into the vagina of a female have been heretofore known in the art, being shown, for example, in U.S. Pat. Nos. 2,507,858, issued to Arnold Kegal; 2,541,520, issued to Arnold Kegal; 3,598,106, issued to Eric Buning; 3,726,273, issued to Ned S. Cole; 4,048,985, issued to Howard A. Sasse; 4,050,449, issued to Frank S. Castellana, et al; 4,106,489, issued to Kenneth W. Martin; and 4,216,783, issued to Howard Kaiser.

Exercise devices of the aforementioned type, which have been heretofore known in the art, have commonly had several inherent disadvantages, such as, for example, being difficult to insert into the vagina; being painful to insert into the vagina or being painful in use during exercising of the vaginal muscles; being so constituted and arranged as to create danger of injury to the vagina during insertion thereinto and/or during use therein; or creating a maximum initial pressure against the vaginal walls, which, in the use thereof, can be the cause of injury to damage to such walls, and the like and also because the compositions of such devices are latex or rubber, such materials are irritative to human tissue and difficult to clean and maintain for repetitive use. It is an important object of the present invention to overcome such disadvantages.

Another object of the present invention is to afford a novel exercise device of the aforementioned type, which, when inserted into position of use in a vagina, exerts a soft, yielding minimal pressure or force against the vaginal walls, which force increases as the vaginal muscles are exercised and contract.

A further object of the present invention is to afford a novel exercise device of the aforementioned type, wherein the parts thereof are so constituted and arranged that, in use, the female using the device is able to recognize the degree of muscle activity being exerted by her own sensations.

Another object of the present invention is to afford a novel device of the aforementioned type, which, if desired, may embody a measuring device for indicating the amount of muscle contraction taking place durihg exercise by measurement of the volume of displaced air from the device.

Another object of the present invention is to afford a novel exercise device of the aforementioned type which is practical and efficient in operation, and which may be readily and economically produced commercially.

Other and further objects of the present invention will be apparent from the following description and claims and are illustrated in the accompanying drawing which, by way of illustration, shows a preferred embodiment of the present invention and the principles thereof and what I now consider to be the best mode in which I have contemplated applying these principles. Other embodiments of the invention embodying the same or equivalent principles may be used and structural changes may be made as desired by those skilled in the art without departing from the present invention and the purview of the appended claims.

DESCRIPTION OF THE DRAWINGS

FIG. 1 is a fragmentary, side elevational view of a device embodying the principles of the present invention, to illustrate the presently preferred embodiment of the present invention, and showing the device connected to a vacuum pump or syringe;

FIG. 2 is a view similar to FIG. 1, but showing part of the device in a different position, and showing the vacuum pump in actuated position;

FIG. 3 is a view, similar to FIG. 2, but showing the device being inserted into a vagina;

FIG. 4 is a view similar to FIG. 2, but showing the device inserted into the vagina and in operable position relative thereto;

FIG. 5 is a detail sectional view taken substantially along the line 5—5 in FIG. 1;

FIG. 6 is a fragmentary, side elevational view of a modified form of the present invention;

FIG. 7 is a detail sectional view taken substantially along the line 7—7 in FIG. 6; and FIG. 8 is a fragmentary, side elevational view of the device shown in FIG. 1, showing the device attached to a pressure gauge.

DESCRIPTION OF THE EMBODIMENTS SHOWN HEREIN

An exercise device 1, embodying the principles of the present invention, is shown in the drawings to illustrate the presently preferred embodiment of the present invention.

The exercise device 1 embodies, in general, an elongated rod 2 having a distal end portion 3 and a proximal end portion 4, with a cuff portion 5 mounted on the distal end portion 3, FIGS. 1-4.

The rod 2, preferably, is semi-rigid and flexible-pliable in construction, and may be made of several suitable materials, such as, preferably medical grade silicone which does not react to human tissue. As will be discussed in greater detail presently, in the use of the device 1, the distal end portion 3 of the rod 2, with the cuff 5 attached thereto, is inserted into the vagina of a female, the proximal end portion 4 of the device 1 affording a member by which the device 1 may be manually retained in such position in the vagina. The free end 6 of the distal end portion 3 preferably is rounded, to facilitate such insertion of the device into the vagina, and as protection against injury to the female during such insertion into the vagina and during the time the device is retained therein.

The cuff portion 5 includes a substantially air impervious medical grade silicone cover 7 and a body portion 8 disposed within the cover 7. Both the cover 7 and the body portion 8 are disposed around the distal end portion 3 of the rod 2, preferably in spaced relation to the end 6 thereof.

The cover 7 is flexible and it is preferably made of medical grade silicone or the like. Preferably, it also is elastic for reasons which will hereinafter be discussed in greater detail. Preferably, the cover 7 is comprised of a suitable elastic material such as the aforementioned medical grade silicone.

The cover 7 is tubular in form, and the end portions 9 and 10 thereof are hermetically sealed to the outer surface of the rod 2 by suitable means, such as, for example, beinc vulcanized thereto or by a suitable medical grade cement such as silicone cement, or the like.

The body or sponge portion 8 affords a resilient mass which preferably completely fills the cover 7 between the end portions 9 and 10 thereof and, when the exercise device is disposed in normal inoperative position, outside the vagina, the sponge portion is preferably effective in yieldingly holding the cover 7 in fully expanded position, as shown in FIG. 1. The body or sponge portion 8 may be made of any suitable resilient material, but, preferably, is made of several grades or densities of a spongelike resilient material having a multitutde of interstices spread therethrough, such as, for example, sponge-type silicone or a suitable resilient plastic material, such as, for example, foamed polyurethane, or the like, for a purpose which will be discussed in greater detail presently.

From the foregoing it will be seen that the cuff portion 5 is similar in construction to the cuffs embodied in the tracheal tubes disclosed in U.S. Pat. Nos. 3,640,282 and 3,799,173, issued to Jack M. Kamen.

An elongated passageway 11 extends longitudinally through the rod 2 from the free end 12 of the proximal end portion 4 thereof into the interior of the cuff 5, terminating at its inner end 13 in inwardly spaced relation to the free end 6 of the distal end portion 3. Passageways 14 extend radially outwardly from the passageway 11, through the rod 2 and open outwardly into the interior of the cuff 5 for the purpose which will be discussed in greater detail presently.

An adapter 15, embodying an elongated tubular body member 16 is mounted in the proximal end portion 4 of the rod 2, with one end portion of the body member 16 disposed in the passageway 11, FIGS. 1-4. The adapter 15 also includes a plug 17, attached to the body portion 16 by a flexible strap 18, the plug 17 being movable on the strap 18 between a position wherein it is disposed in the free end portion 19 of the body portion 16 of the adapater 15 to thereby close the passageway 11 and the body portion 16 to the atmosphere, as shown in FIG. 3, and a position wherein it is disposed out of the adapter 15, as shown in FIGS. 1, 2 and 4.

With the exercise device 1 constructed in the aforementioned manner, when it is desired to insert it into a vagina, such as the vagina 20 diagramratically shown in FIGS. 3 and 4, a partial vacuum may be applied to the free end 19 of the adapter 15 by any suitable means, such as, for example, a vacuum syringe P, shown in FIGS. 1 and 2, to thereby cause the cuff portion 5 to move from its normal expanded position, shown in FIG. 1, to a collapsed position as shown in FIGS. 2 and 3. After the cuff portion 5 has thus been collapsed, the passageway through the adapter 15 and the passageways 11 and 14, into the interior of the cuff 5, may be closed by any suitable means, such as, for example, by first pinching tubular member 16 to close the same, then withdrawing the syringe P from the adapter 15, and immediately closing the end portion 19 of the tubular member 16 by a finger, or the like. However, in the preferred form of the present invention, such closing of the end portion 19 is effected by inserting the plug 17 thereinto, as shown in FIG. 3. This, it will be seen, is effective to retain the partial vacuum in the cuff 5 and, therefore, retain it in the collapsed position shown in FIGS. 2 and 3.

While thus maintaining the vacuum on the cuff 5, the distal end portion 3 and the cuff 5 may be inserted into a vagina, such as the vagina 20, FIG. 3, the collapsed position of the cuff 5 facilitating such insertion. Preferably, this insertion of the device 1 is such that the cuff 5 is disposed in position within the sphincter type muscles in the vaginal area. Thereafter, when the device 1 has been moved into the desired position in the vagina 20, the partial vacuum in the cuff 5 may be released to thereby permit the cover 7 to be pushed and expanded outwardly by the expansion of the resilient sponge body member 8. The expansion of the cover 7 is from the collapsed position to a position wherein it is yieldingly positioned within the body portion 8 in engagement with the inner wall 21 of the vagina 20, FIG. 4. Such movement and expansion, it will be seen, is caused by the resiliency of the sponge body portion 8 and is a direct result of the volumetric expansion thereof. Importantly, the density of the sponge body portion 8 may be varied to provide different grades or amounts of yielding pressure gradients within each exercise device. This is to be distinguished from the expansion of the aforementioned cuffs on exercise devices heretofore known in the art, which cuffs are expanded by the application of a positive pressure, by the introduction of air or other working fluid thereinto under pressure. Such devices therefore start with the largest force upon initial contact with the vaginal muscles.

It will be remembered that the cover 7 of the cuff 5 may be made of any suitable flexible material, but preferable is medical grade silicone. When so constructed, the cover comprised of medical grade silicone is so constructed that the wrinkles that are formed therein when in the collapsed position, as shown in FIGS. 2 and 3, are soft and minimize abrasive tendencies to the vaginal lining or mucosa. Whereas with some materials which are flexible but do not possess softness and which are abrasive, such as, for example, certain plastic or rubber sheet materials, and the like, wrinkles could be formed when the cover 7 is disposed in a position wherein it was extended outwardly less than that which it occupies when in fully extended position. In the present invention it is not essential as to whether or not the cover 7 is wrinkled when the cuff 5 is in fully collapsed position, as shown in FIGS. 2 and 3, and it is not essential nor an absolute requirement, when the cuff 5 is disposed in operative engagement with the walls of a vagina, such as is shown in FIG. 4, that the cover 7 be wrinkle free. However, it is preferred that the cover 7 be structured and sized to substantially envelope the sponge portion 8, when the cuff 5 is in operative engagement with a vagina, as shown in FIG. 4. Therefore, to insure against such abrasive wrinkles, I prefer that the cover 7 be made of a suitable material such as medical grade silicone.

With device 1 thus disposed in operative position in the vagina of a female, the female may contract her pelvic floor muscles against the urging of the body portion 8 of the cuff 5. This, it will be seen, is a gentle, yielding urging, which, unlike the urging of the fluids used to inflate cuffs of exercise devices heretofore known in the art with a positive pressure which cannot be compressed, does not exert a positive pressure against the sidewalls of the vagina, which positive pressure is in danger of injuring delicate membranes such as the sidewalls of the vagina. Instead, the present invention begins with a minimal resistive force which increases as contraction increases that is, the cuff require increasing muscle force to increase the compression or resistive force, thus resulting in a resistive exercise.

It is important to note that the use of the device 1, in pelvic floor muscle exercise, provides not only a resistive exercise for such muscles, but also provides progressively increasing resistance as the body portion 8 of the cuff 5 continues to be compressed. Thus, it will be seen that the device 1 is capable of exerting a small minimal resistive force at the beginning of an exercise program, when the muscular tone and strength is relatively weak, while affording a gradually increasing resistive force as the muscular tone and strength increases. Also, with this increasing compression by the body portion 8 of the cuff 5, the female using the device is able to recognize this increasing resistance by her own sensations, and thus realize that the exercises are being effective in building up the tone and strength of her pelvic floor muscles.

At the completion of the exercises, the device 1 may be manually removed from the vagina. Preferably, prior to such removal, a partial vacuum is again applied to the cuff 5 in the aforementioned manner, to thereby dispose the cuff 5 in partially or totally collapsed position, as shown in FIGS. 2 and 3, to facilitate removal of the device 1.

Although the rod 2 is shown in FIGS. 1-5 of the drawings as embodying the passageway 11 as an integral part thereof, it will be appreciated by those skilled in the art that this is merely by way of illustration of the preferred embodiment of the present invention, and not by way of limitation, and that other passageways may be afforded without departing from the purview of the broader aspects of the present invention. For example, instead of the rod 2, a solid semi-rigid but flexible rod 2a, as shown in FIGS. 6 and 7, may be used, and a separate tube, such as a tube 22, having a passageway 11a therethrough may be substituted therefor.

Also, it will be seen that, with the device 1 constituted and arranged in the aforementioned manner, if it is desired to do so a measuring device may be associated therewith for measuring the performance of the female in contracting her pelvic floor muscles, rather than the aforementioned reliance on her own sensations as to the increasing resistance of the body portion 8. For example, as illustrated in FIG. 8, a volume displacement measuring device, such as an air gauge means 23, may be secured to the end portion 19 of the tubular body portion 16 of the adapter 15 by a suitable conduit, such as a tube 24, the gauge 23 being capable of measuring the air flow from within the cuff 5, the passageway 11 and the adapter 12 caused by the contraction of the vaginal muscles of the female, greater contraction, of course, causing higher air flow. If desired, the user of the device can even place a finger adjacent to the opening 19 and physically feel and sense the air flow upon contraction of the vaginal muscles.

From the foregoing it will be seen that the present invention affords a novel device for use in exercising the vaginal muscles of a female.

In addition, it will be seen that the present invention affords a novel device of the aforementioned type which is practical and efficient in operation, and which may be readily and economically produced commercially.

Thus, while I have illustrated and described the preferred embodiments of my invention, it is to be understood that these are capable of variation and modification, and I therefore do not wish to be limited to the precise details set forth, but desire to avail myself of such changes and alterations as fall within the purview of the following claims.

I claim:

1. A resistive exercise device for exercising the vaginal muscles comprising
   a. an elongated rod having
      (1) a closed distal end portion for insertion into the vagina of a female, and
      (2) a proximal end portion for manually retaining said distal end portion in said vagina,
   b. a cuff mounted on said distal end portion
   c. said cuff comprising
      (1) a flexible tubular cover
         (a) disposed on said elongated rod in surrounding relation thereto, and
         (b) having its ends secured to the outer surface of said rod, and
      (2) a resilient body portion mounted between said cover and said rod at said distal end,
   d. said body portion having normally an expanded position, wherein it is effective to hold a portion of said cover outwardly away from said rod under atmospheric conditions,
   e. means operatively connected to said cover for
      (1) creating a vacuum therein and thereby move said cover inwardly from said expanded position for movement of said distal end portion and said cuff into said vagina, and
      (2) releasing such a vacuum in said cover to thereby permit said body portion of said cuff to expand outwardly to move said cover outwardly toward said expanded position to
         (a) yieldinly engage the walls of the vagina in which said distal end portion and said cuff are disposed to provide a minimal resistive force against the walls of the vagina, and
         (b) to be collapsed inwardly by said walls, against the urging of said resilient body portion, upon contraction of the vaginal muscles by said female,
f. said means connected to said cover comprises a passageway extending longitudinally of said rod from said proximal end into said cover for passage of air therethrough during said creation and release of said vacuum, and
g. a volume displacement indicator means operatively connected to said cover for measuring the amount of air flow from within the cuff resulting from the force with which said cover is collapsed by said contraction of said vaginal muscles.

2. A device as defined in claim 1, and in which
a. said body portion has inerstices spread therethrough.

3. A device as defined in claim 1, and in which
a. said body portion comprises a spongelike elastic mass mounted in said cover for yieldingly urging the latter outwardly.

4. A device as defined in claim 3, and in which
a. said elastic means comprises polyurethane foam rubber, and
b. said cover comprises medical grade silicone.

5. A device as defined in claim 1, and which includes
a. means for closing said passageway for thereby holding said vacuum in said cover during insertion of said distal end portion and said cuff into said vagina.

6. A device as defined in claim 5, and in which
a. said means for closing said passageway comprises a plug attached to said proximal end and movable into and out of said passageway.

7. A device as defined in claim 1, and which said rod is flexible and pliable.

* * * * *

UNITED STATES PATENT AND TRADEMARK OFFICE
CERTIFICATE OF CORRECTION

PATENT NO. : 4,653,514

DATED : March 31, 1987

INVENTOR(S) : Seymour W. Shapiro

It is certified that error appears in the above-identified patent and that said Letters Patent is hereby corrected as shown below:

Column 8, line 5, "means" should read -- mass --.

Signed and Sealed this

First Day of September, 1987

Attest:

DONALD J. QUIGG

Attesting Officer

Commissioner of Patents and Trademarks